United States Patent
Torenbeek et al.

[11] Patent Number: 5,808,110
[45] Date of Patent: Sep. 15, 1998

[54] CYCLIC KETONE PEROXIDE FORMULATIONS

[75] Inventors: Reinder Torenbeek, Terwolde; John Meijer, Deventer; Andreas Herman Hogt, Enschede; Gerrit Bekendam, Wierden, all of Netherlands

[73] Assignee: Akzo Nobel nv, Arnhem, Netherlands

[21] Appl. No.: 776,178

[22] PCT Filed: Jul. 14, 1995

[86] PCT No.: PCT/EP95/02830

§ 371 Date: Mar. 13, 1997

§ 102(e) Date: Mar. 13, 1997

[87] PCT Pub. No.: WO96/03397

PCT Pub. Date: Feb. 8, 1996

[30] Foreign Application Priority Data

Jul. 21, 1994 [EP] European Pat. Off. .............. 94202136

[51] Int. Cl.$^6$ ................................. C07D 325/00
[52] U.S. Cl. ......................... 549/352; 549/357; 549/435
[58] Field of Search ................... 549/357, 352, 549/435

[56] References Cited

U.S. PATENT DOCUMENTS

| | | | |
|---|---|---|---|
| 3,003,000 | 10/1961 | Milas | 260/610 |
| 3,649,546 | 3/1972 | McCloskey et al. | 252/186 |
| 3,867,461 | 2/1975 | Leveskis et al. | 260/610 |
| 4,271,279 | 6/1981 | Pastorino et al. | 525/387 |
| 4,299,718 | 11/1981 | Conti et al. | 252/106 |

FOREIGN PATENT DOCUMENTS

| | | | |
|---|---|---|---|
| 0 209 181 | 1/1987 | European Pat. Off. | 179/87 |
| 0 355 733 | 2/1990 | European Pat. Off. | C07C 409/40 |
| 2 193 840 | 2/1974 | France | C08F 22/00 |
| 2 316 226 | 1/1977 | France | C07C 179/06 |
| 827511 | 2/1960 | United Kingdom . | |
| 912061 | 12/1962 | United Kingdom . | |
| 1072728 | 6/1967 | United Kingdom | C07C 73/00 |
| 1 442 681 | 7/1976 | United Kingdom | C08F 8/50 |

OTHER PUBLICATIONS

*International Search Report*, dated Oct. 5, 1995.
*Uhlmann 3rd Edition*, (1962) Vo. 13, Peroxyde, organische, pp. 256–257.
*Journal of American Chemical Society*, vol. 81,, pp. 5824–5826 (1959).
*Houben–Weyl Methoden de Organische Chemie*, E13, vol. 1, p. 736, English translation attached 2 pages. (1973).
*Organic Peroxides*, Wiley–Interscience, vol. III, pp. 67–87. (1978).

Primary Examiner—James H. Reamer
Attorney, Agent, or Firm—Ralph J. Mancini

[57] ABSTRACT

A transportable, storage stable cyclic ketone peroxide composition which comprises 1.0–90% by weight of one or more cyclic ketone peroxides and 10–99% by weight of one or more diluents selected from the group consisting of liquid phlegmatizers for the cyclic ketone peroxides, plasticizers, solid polymeric carriers, inorganic supports, organic peroxides and mixtures thereof, is disclosed. Also disclosed is the use of these cyclic ketone peroxide formulations in the modification of (co)polymers. These formulations provide a surprising degree of polymer modification when compared to their non-cyclic ketone peroxide counterparts.

9 Claims, No Drawings

CYCLIC KETONE PEROXIDE FORMULATIONS

FIELD OF THE INVENTION

The present invention relates to cyclic ketone peroxide formulations and to the use of these cyclic ketone peroxide formulations for the modification of (co)polymers.

BACKGROUND OF THE INVENTION

Several formulations of ketone peroxides are known from the prior art. For example, British Patent 827,511 discloses formulations of ketone peroxides in paraffinic diesel oil. These formulations may include cyclic ketone peroxides though the goal of this publication is to minimize the amount of cyclic peroxide present in the compositions and thus such compositions contain only minor amounts of cyclic ketone peroxides.

British Patent 912,061 discloses formulations of ketone peroxides in dimethyl phthalate and paraffinic diesel oil. Again, formulations containing only minor amounts of cyclic ketone peroxides are disclosed.

British Patent 1,072,728 discloses stabilized ketone peroxide compositions formulated in safety solvents which are selected from alcohols and glycols. Such compositions optionally contain diluents other than the safety solvents, such diluents being phthalate esters. These ketone peroxide formulations also contain only minor proportions of cyclic ketone peroxides.

U.S. Pat. No. 3,649,546 relates to non-hazardous ketone peroxide polymerization initiators wherein ketone peroxides are formulated in esters with boiling points in the range of 140°–250° C. Such compositions may also contain other diluents which are often incorporated into ketone peroxide compositions. Again, these ketone peroxide formulations contain only minor amounts of cyclic ketone peroxides.

U.S. Pat. No. 3,867,461 also relates to non-hazardous ketone peroxide compositions. These compositions are desensitized with a heat-desensitizing solvent having a boiling point between 185°–225° C. and a stabilizer selected from vinyl pyrrolidone and polyvinyl pyrrolidone. The ketone peroxides contained in these compositions are primarily non-cyclic ketone peroxides.

U.S. Pat. No. 4,299,718 relates to peroxide mixtures which comprise ketone peroxides formulated in a solvent, optionally with a phlegmatizer. Again, these compositions comprise only minor amounts of cyclic ketone peroxides present as an impurity in the composition.

Finally, European Patent Application EP-A-0209181 relates generally to desensitized ketone peroxide compositions which contain, as a desensitizing agent, 2,2,4-trimethyl-1,3-pentanediol diisobutyrate and the use of these ketone peroxide compositions to manufacture foundry cores or moulds. These ketone peroxides are also predominantly non-cyclic.

Until now, ketone peroxides were primarily employed in the curing of unsaturated polyester resins. In this application, it is desirable to minimize the quantity of cyclic ketone peroxide present in the composition as is taught by British Patent 827,511 since these peroxides are considered to be less active for this application.

The present inventors have unexpectedly found that cyclic ketone peroxide formulations possess a high activity in (co)polymer modification processes despite the fact that it was thought that these peroxides were less active than their non-cyclic counterparts.

Accordingly, it is the primary object of the present invention to provide safe, storage stable cyclic ketone peroxide formulations which can be employed in (co)polymer modification processes. This and other objects of the invention will be apparent from the summary and detailed descriptions which follow.

SUMMARY OF THE INVENTION

In a first aspect, the present invention relates to a transportable, storage stable peroxide composition which comprises 1.0–90% by weight of one or more cyclic ketone peroxides selected from peroxides represented by the formulae I–III:

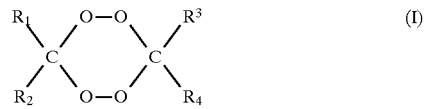

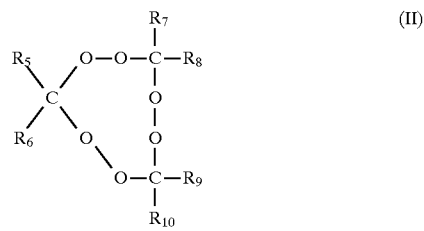

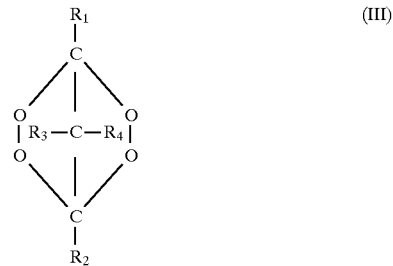

wherein $R_1$–$R_{10}$ are independently selected from the group consisting of hydrogen, $C_1$–$C_{20}$ alkyl, $C_3$–$C_{20}$ cycloalkyl, $C_6$–$C_{20}$ aryl, $C_7$–$C_{20}$ aralkyl and $C_7$–$C_{20}$ alkaryl, which groups may include linear or branched alkyl moieties; and each of $R_1$–$R_{10}$ may be optionally substituted with one or more groups selected from hydroxy, $C_1$–$C_{20}$ alkoxy, linear or branched $C_1$–$C_{20}$ alkyl, $C_6$–$C_{20}$ aryloxy, halogen, ester, carboxy, nitrile, and amido; and 10–99% by weight of one or more diluents selected from the group consisting of liquid phlegmatizers for the cyclic ketone peroxides, plasticizers, solid polymeric carriers, inorganic supports, organic peroxides and mixtures thereof, with the proviso that when said diluent comprises a non-cyclic ketone peroxide, at least 20% of the total active oxygen content of the formulation must be attributable to one or more cyclic ketone peroxides of the formulae I–III.

In a second aspect, the present invention relates to the use of these peroxide formulations in the modification of (co) polymers.

It has been unexpectedly found that formulations of the peroxides of the formulae I–III perform at least as well as commercially available peroxides used in polymer modification and that they provide a performance which is superior to formulations of their non-cyclic dialkyl ketone peroxide counterparts.

DETAILED DESCRIPTION OF THE INVENTION

The peroxides of the formulae I–III can be made by reacting a ketone with hydrogen peroxide as is described in U.S. Pat. No. 3,003,000; Uhlmann, 3rd Edition, Vol. 13, pp. 256–57 (1962); the article, "Studies in Organic Peroxides. XXV. Preparation, Separation and Identification of Peroxides Derived from Methyl Ethyl Ketone and Hydrogen Peroxide," Milas, N. A. and Golubovic, A., *J. Am. Chem. Soc.*, Vol. 81, pp. 5824–26 (1959), *Organic Peroxides*, Swern, D. editor, Wiley-Interscience, New York (1970) and Houben-Weyl Methoden der Organische Chemie, E13, Volume 1, page 736, the disclosures of which are hereby incorporated by reference.

Suitable ketones for use in the synthesis of the present peroxides include, for example, acetone, acetophenone, methyl-n-amyl ketone, ethylbutyl ketone, ethylpropyl ketone, methylisoamyl ketone, methylheptyl ketone, methylhexyl ketone, ethylamyl ketone, diethylketone, dipropyl ketone, methylethyl ketone, methylisobutyl ketone, methylisopropyl ketone, methylpropyl ketone, methyl-n-butyl ketone, methyl-t-butyl ketone, isobutylheptyl ketone, diisobutyl ketone, 2,4-pentanedione, 2,4-hexanedione, 2,4-heptanedione, 3,5-heptanedione, 3,5-octanedione, 5-methyl-2,4-hexanedione, 2,6-dimethyl-3,5-heptanedione, 2,4-octanedione, 5,5-dimethyl-2,4-hexanedione, 6-methyl-2,4-heptanedione, 1-phenyl-1,3-butanedione, 1-phenyl-1,3-pentanedione, 1,3-diphenyl-1,3-propanedione, 1-phenyl-2,4-pentanedione, methylbenzyl ketone, phenylmethyl ketone, phenylethyl ketone, methylchloromethyl ketone, methylbromomethyl ketone and coupling products thereof. Preferred peroxides of the formulae I–III are those in which $R_1$–$R_{10}$ are independently selected from $C_1$–$C_{12}$ alkyl groups. Of course, other ketones having the appropriate R groups corresponding to the peroxides of the formulae I–III can be employed, as well as mixtures of two or more different ketones.

Examples of preferred peroxides of the formulae I–III for use in accordance with the present invention are the cyclic ketone peroxides derived from acetone, methylamyl ketone, methylheptyl ketone, methylhexyl ketone, methylpropyl ketone, methylbutyl ketone, diethyl ketone, methylethyl ketone methyloctyl ketone, methylnonyl ketone, methyldecyl ketone, methylundecyl ketone, and mixtures thereof.

The peroxides can be prepared, transported, stored and applied in the form of powders, granules, pellets, pastilles, flakes, slabs, pastes, solid masterbatches and solutions. These formulations may optionally be phlegmatized, as necessary, depending on the particular peroxide and its concentration in the formulation. Which of these forms is to be preferred partly depends on the application for which it will be used and partly on the manner that it will be mixed. Also, considerations of safety may play a role to the extent that phlegmatizers may have to be incorporated in certain compositions to ensure their safety.

Cyclic ketone peroxides are composed of at least two ketone peroxide entities which may be the same or different. Thus, cyclic ketone peroxides may exist in the form of dimers, trimers, etc. When cyclic ketone peroxides are prepared, usually a mixture is formed which predominantly exists of the dimeric and trimeric forms. The ratio between the various forms mainly depends on the reaction conditions during the preparation. If, desired, the mixture may be separated in the individual cyclic ketone peroxide compounds. Generally, the cyclic ketone peroxide trimers are less volatile and more reactive than the corresponding dimers. Preference for certain compositions or individual compounds may depend on differences in physical properties or requirements in application of the peroxides, e.g. storage stability, half-life time vs. temperature, volatility, boiling point, solubility, etc. It is to be understood that any form of the cyclic ketone peroxides, e.g. oligomeric compounds or mixtures, are comprised in the present invention.

In order to clearly distinguish the present cyclic ketone peroxide formulations from prior art ketone peroxide formulations which contained some cyclic ketone peroxides as an impurity therein, it is required that at least 20% of the total active oxygen content in the formulations of the present invention be attributable to one or more cyclic ketone peroxide(s) of the formulae I–III. Comparative examples included herein demonstrate the advantages of these formulations of cyclic ketone peroxides over formulations of their non-cyclic counterparts.

The formulations of the present invention are transportable, storage stable and contain 1.0–90%, by weight, of one or more cyclic ketone peroxides selected from the formulae I–III above. By transportable is meant that the formulations of the present invention have passed the pressure vessel test (PVT). By storage stable is meant that during a reasonable storage period under standard conditions the formulations of the present invention are both chemically and physically stable.

More preferred formulations in accordance with the present invention contain 10–70% by weight of one or more of the cyclic ketone peroxides of the formulae I–III above and most preferably these formulations contain 20–60% by weight of the cyclic ketone peroxides.

The formulations of the present invention can be liquids, solids or pastes depending on the melting point of the peroxide and the diluent which is employed. Liquid formulations can be made using, as the diluent, liquid phlegmatizers for the cyclic ketone peroxides, liquid plasticizers, organic peroxides and mixtures thereof. The liquid component is generally present in an amount of 10–99% of the composition, more preferably 30–90% and most preferably, 40–80% of the liquid formulation consists of liquid diluents.

It should be noted that certain phlegmatizers may not be suitable for use with all of the ketone peroxides of the present invention. More particularly, in order to obtain a safe composition, the phlegmatizer should have a certain minimum flash point and boiling point relative to the decomposition temperature of the ketone peroxide such that the phlegmatizer cannot be boiled off leaving a concentrated, unsafe ketone peroxide composition behind. Thus, the lower boiling phlegmatizers mentioned below may only be useful, for example, with particular substituted ketone peroxides of the present invention which have a low decomposition temperature.

Examples of useful liquid phlegmatizers for the cyclic ketone peroxides include various solvents, diluents and oils. More particularly, useful liquids include alkanols, cycloalkanols, alkylene glycols, alkylene glycol monoalkyl ethers, cyclic ether substituted alcohols, cyclic amides, aldehydes, ketones, epoxides, esters, hydrocarbon solvents, halogenated hydrocarbon solvents, paraffinic oils, white oils and silicone oils.

Examples of esters include, but are not limited to, monocarboxylic esters of mono- and dihydric alcohols, dicarboxylic acid esters of monohydric alcohols, carbonates of monohydric alcohols, alkoxyalkyl esters, β-keto esters, phthalates, phosphates, benzoates, adipates and citrates.

More specific examples of esters useful in the formulations of the present invention are dimethyl phthalate, dibutyl phthalate, dioctyl phthalate, dibenzyl phthalate, butyl benzyl phthalate, diallyl phthalate, n-pentyl acetate, isopentyl acetate, n-hexyl acetate, 2-ethylhexyl acetate, benzyl acetate, methyl benzoate, ethyl benzoate, isopropyl benzoate, n-octyl benzoate, isodecyl benzoate, n-butyl pivalate, isoamyl pivalate, sec-amyl pivalate, n-hexyl pivalate, dioctyl adipate, diisodecyl adipate, methyl neodecanoate, n-butyl neodecanoate, propylene glycol diacetate, ethylene glycol diacetate, cyclohexyl acetate, neopentyl acetate, methyl-2-ethylhexanoate, n-heptyl formate, n-octyl formate, dipropyl carbonate, dibutyl carbonate, isoamyl propionate, sec-amyl propionate, benzyl propionate, butyl caproate, ethylene glycol dipropionate, heptyl propionate, methylphenyl acetate, octyl acetate, 2-ethylhexyl acetate, propyl caprylate, triethyl phosphate, tricresyl phosphate, trixylyl phosphate, cresyl diphenyl phosphate, 2-ethylhexyl-diphenyl phosphate, isodecyl-diphenyl phosphate, tri(2-ethylhexyl) phosphate, dimethyl methylphosphonate, chlorinated phosphate esters, tributyl phosphate, tributoxyethyl phosphate, methyl decanoate, dimethyl succinate, diethyl succinate, dimethyl malonate, diethyl malonate, methylethyl succinate, diisobutyl nylonate, 2,2,4-trimethyl-1,3-pentanediol, diethyl oxalate, methyl p-toluate and acetyltributyl citrate.

Useful hydrocarbon solvents include, but are not limited to, hydrogenated oligomers of alkanes such as Isopar® products (ex. Exxon), pentane, heptane, isododecane, amyl benzene, isoamyl benzene, decalin, o-diisopropyl benzene, m-diisopropyl benzene, n-dodecane, 2,4,5,7-tetramethyl octane, n-amyl toluene, 1,2,3,4-tetramethyl benzene, 3,5-diethyl toluene and hexahydronaphthalene. Useful halogenated hydrocarbons include phenyl trichloride, 3-bromo-o-xylene, 4-bromo-o-xylene, 2-bromo-m-xylene, 4-bromo-m-xylene, 5-bromo-m-xylene, o-dibromobenzene, p-dibromobenzene, 1,4-dibromobutane, 1,1-dibromo-2,2-dichloroethane, bromooctane, tetrabromoethylene, 1,2,3-trichlorobenzene and 1,2,4-trichlorobenzene.

Examples of aldehydes useful in the formulations of the present invention include n-chlorobenzaldehyde and decanal. Examples of ketones useful in the formulations of the present invention include acetophenone, isophorone, isobutyl ketone, methylphenyl diketone, diamyl ketone, diisoamyl ketone, ethyloctyl ketone, ethylphenyl ketone, acetone, methyl-n-amyl ketone, ethylbutyl ketone, ethylpropyl ketone, methylisoamyl ketone, methylheptyl ketone, methylhexyl ketone, ethylamyl ketone, dimethyl ketone, diethyl ketone, dipropyl ketone, methylethyl ketone, methylisobutyl ketone, methylisopropyl ketone, methylpropyl ketone, methyl-t-butyl ketone, isobutylheptyl ketone, diisobutyl ketone, 2,4-pentanedione, 2,4-hexanedione, 2,4-heptanedione, 3,5-heptanedione, 3,5-octanedione, 5-methyl-2,4-hexanedione, 2,6-dimethyl-3,5-heptanedione, 2,4-octanedione, 5,5-dimethyl-2,4-hexanedione, 6-methyl-2,4-heptanedione, 1-phenyl-1,3-butanedione, 1-phenyl-1,3-pentanedione, 1,3-diphenyl-1,3-propanedione, 1-phenyl-2,4-pentanedione, methylbenzyl ketone, phenylethyl ketone, methylchloromethyl ketone, methylbromomethyl ketone and coupling products thereof. An example of an epoxide which may be employed in the formulations of the present invention is styrene oxide.

Examples of alcohols useful in the formulations of the present invention are n-butyl alcohol, capryl alcohol, octyl alcohol, dodecyl alcohol, tetrahydrofurfuryl alcohol, 1,4-dihydroxymethyl cyclohexane, cyclohexanol, glycerol, ethylene glycol, polyethylene glycols with molecular weights under 20,000, propylene glycol, dipropylene glycol, neopentyl glycol, hexylene glycol, 1,4-butylene glycol, 2,3-butylene glycol, butene diol, 1,5-pentane diol, 3,6-dimethyloctane-3,6-diol, 2,5-dimethyl-hex-3-yne-2,5-diol, 2,4,7,9-tetramethyldecane-4,7-diol, 2,2,4,4-tetramethyl-1,3-cyclobutanediol, ethylene glycol monoethyl ether, ethylene glycol monobutyl ether, diethylene glycol monoethyl ether, diethylene glycol monobutyl ether, diethylene glycol dibenzoate, dipropylene glycol dibenzoate, propylene glycol dibenzoate, 2-pyrrolidone and N-methyl pyrrolidone.

The paraffinic oils useful in the formulations of the present invention include, but are not limited to, halogenated paraffinic oils and paraffinic diesel oil. Other oils, including white oils, epoxidized soybean oils and silicone oils, are also useful in the formulations of the present invention.

Examples of organic peroxides useful in the formulations of the present invention include methylethyl ketone peroxide, methylisobutyl 2,5-bis(tertiarybutylperoxy)-2,5-dimethylhexane, bis(t-butylperoxyisopropyl)benzene and 2,5-bis(t-butylperoxy)-2,5-dimethyl-3-hexyne.

In the solid and/or paste formulations of the present invention, solid carrier materials are employed. Examples of such solid carriers are low-melting solids such as dicyclohexylphthalate, dimethyl fumarate, dimethylisophthalate, triphenylphosphate, glyceryltribenzoate, trimethylolethane tribenzoate, dicyclohexylterephthalate, paraffinic waxes and dicyclohexylisophthalate; polymers and inorganic supports. Inorganic supports include materials such as fumed silica, precipitated silica, hydrophobic silica, chalk, whiting, surface-treated clays such as silane-treated clays, calcined clays and talc.

Polymers useful in the formulations of the present invention include polymers such as polyethylene, polypropylene, ethylene/propylene copolymers, ethylene/propylene/diene monomer terpolymers, chlorosulphonated polyethylene, chlorinated polyethylene, polybutylene, polyisobutylene, ethylene/vinyl acetate copolymers, polyisoprene, polybutadiene, butadiene/styrene copolymers, natural rubber, polyacrylate rubber, butadiene/acrylonitrile copolymers, acrylonitrile/butadiene/styrene terpolymers, silicone rubber, polyurethanes, polysulphides, solid paraffins and polycaprolactone.

Storage stable formulations must be both physically and chemically stable. By physically stable formulations is meant formulations which do not suffer from significant phase separation upon storage. The physical stability of the present formulations can, in some instances, be improved by addition of one or more thixotropic agents selected from cellulose esters, hydrogenated castor oil and fumed silica. Examples of such cellulose esters are the reaction products of cellulose and acid compounds selected from, for example, acetic acid, propionic acid, butyric acid, phthalic acid, trimellitic acid and mixtures thereof. Examples of commercially available hydrogenated castor oils are Rheocin® (ex. Sud-Chemie), Thixcin® (ex. Rheox Inc.) and Luvotix® (ex. Lehmann & Voss). Examples of commercially available fumed silicas include Aerosil® (ex. Degussa), Cab-O-Sil® (ex. Cabot) and HDK® (ex. Wacker Chemie).

By chemically stable formulations is meant formulations which do not lose a significant amount of their active oxygen content upon storage. The chemical stability of the present formulations can, in some instances, be improved by addition of one or more known additives including sequestering agents such as dipicolinic acid and/or antioxidants such as 2,6-di(t-butyl)-4-methyl phenol and para-nonyl phenol.

The formulations of the present invention may also contain optional other additives as long as these additives do not have a significant negative effect on the transportability and/or storage stability of the formulations. As examples of such additives may be mentioned: anti-caking agents, free-flowing agents, anti-ozonants, antioxidants, anti-degradants, U.V. stabilizers, coagents, fungicides, antistats, pigments, dyes, coupling agents, dispersing aids, blowing agents, lubricants, process oils and mould-release agents. These additives may be employed in their usual amounts.

The formulations of the present invention are useful in conventional (co)polymer modification processes for the cross-linking, degradation or other types of modification of (co)polymers.

The present invention will be further illustrated by the following examples.

EXAMPLES

Materials Employed

Polymers Polypropylene Homopolymer (Hostalen® PPUO180P ex. Hoechst). Polypropylene Homopolymer (ex. Himont) (Moplen® FLS20). Porous Polypropylene Powder (Accurel® EP100SR, ex. Akzo Fibers & Polymers).

Peroxides—2,5-bis(tert-butylperoxy)-2,5-dimethylhexane
  assay 95.35% (Trigonox® 101, ex. Akzo Chemicals) [Theoretical Active Oxygen Content 11.0%].
  Methylethyl Ketone Peroxide (Butanox® LPT, ex. Akzo Chemicals)[Total Active Oxygen Content 8.5%].
  Methylethyl Ketone Peroxide (MEKP-T3).
  Cyclic Methylethyl Ketone Peroxide (MEKP-cyclic) [Total Active Oxygen Content 10.63%].
  Methylisobutyl Ketone Peroxide (Trigonox® 233, ex. Akzo Chemicals)[Total Active Oxygen Content 8.04% of which 1.2% is derived from cyclic ketone peroxides].
  Cyclic Methylisobutyl Ketone Peroxide (MIBKP-cyclic) [Total Active Oxygen Content 8.03%].
  Cyclic Methylisopropyl Ketone Peroxide (MIPKP-cyclic) [Total Active Oxygen Content 7.86%].
Miscellaneous: Irganox® 1010 (hindered phenol antioxidant—ex. Ciba-Geigy)
  Isododecane Solvent
  Primol® 352 white oil (ex. Exxon)
  Ketjensil® SM300 silica (ex. Akzo Chemicals)

Measurement of the Melt Flow Index

The Melt Flow Index (MFI) was measured with a Göttfert® Melt Indexer Model MP-D according to DIN 53735/ASTM 1238 (230° C., 21.6N load).

Measurement of the Total Active Oxygen Content

The total active oxygen content was measured by placing 50 ml of glacial acetic acid in a 250 ml round-bottomed flask fitted with a ground glass joint, an inlet tube for nitrogen gas, a heating mantle and a 70 cm. long air condensor. Nitrogen gas was then passed over the liquid with heating until the liquid boiled. After 2 minutes of boiling, 5 ml of 770 g/l potassium iodide solution was added and a sample containing approximately 2 meq of active oxygen was added to the reaction mixture with mixing. The air condensor was then connected and the contents of the flask were heated rapidly to boiling and maintained at moderate boiling for 30 minutes. 50 ml of water was then added through the condensor and the condensor was removed from the flask. The reaction mixture was then immediately titrated with a 0.1N sodium thiosulphate solution until the yellow color disappeared. A blank should be run alongside this titration.

The total active oxygen may then by calculated by subtracting the volume of sodium thiosulphate solution used in the blank from the amount used in the titration, multiplying this figure by the normality of the sodium thiosulphate solution and then by 800, and finally dividing by the mass of the peroxide sample in milligrams.

The active oxygen content of the non-cyclic peroxides used was measured by placing 20 ml of glacial acetic acid in a 200 ml round-bottomed flask fitted with a ground glass joint and an inlet tube for nitrogen gas. Nitrogen gas was then passed over the surface of the liquid. After 2 minutes, 4 ml of 770 g/l potassium iodide solution was added and a sample containing approximately 1.5 meq of active oxygen was added to the reaction mixture with mixing. The reaction mixture was allowed to stand for at least 1 minute at 25° C.±5° C. The reaction mixture was then titrated with a 0.1N sodium thiosulphate solution to colorless end point adding 3 ml of 5 g/l starch solution towards the end of the titration. A blank should be run alongside this titration.

Determination of the dimer/trimer (D/T) ratio by GC-analysis

Equipment: Hewlett Packard 5890
Column: CP Sil 19CB
Diameter: 0.32 μm
Thickness: 0.20 μm
Length: 25 m
Detector: FID
Tinj: 100° C.
Tdet: 300° C.
Range: 4
Attenuation: 1
Temperature program: 40° C. (2 min.), 8° C./min. to 280° C. (10 min.)

The Pressure Vessel Test (PVT)

A stainless steel vessel type AISI 316 is fitted with an aperture disk having a 9.0 mm. orifice and a thickness of 2.0±0.2 mm. Into the orifice is fitted a bursting disk of brass having a thickness of 0.55 mm and capable of withstanding a bursting pressure of 5.4±0.5 bar at room temperature. Rolled brass containing 67% copper is a suitable material for the bursting disk.

The pressure vessel is then placed on a tripod inside a protective cylinder and a heating device, such as a butane burner, having a heat output of about 2,700 Kcal/hour is placed under the pressure vessel such that the flame just touches the bottom of the vessel. The test area should be isolated for safety reasons by, for example, concrete walls provided with an armored glass viewing port.

In the test, 10.0 grams of the peroxide formulation are placed evenly over the bottom of the pressure vessel. The bursting disk and retaining ring are then put into place and the bursting disk is covered with enough water to keep it a low temperature. The burner is then lit and placed under the pressure vessel. The test is allowed to run until the decomposition reaction has ceased as evidenced by an explosion or the end of hissing and/or smoke production or extinction of the flame in the pressure vessel. If there is no explosion using a 9.0 mm. orifice, then the formulation is considered to be transportable.

Synthesis Examples

Preparation of MEKP-T3 in Isododecane (Composition I)
  To a stirred mixture of 21.6 g. of methylethyl ketone, 22.5 g. isododecane and 5.9 g. of a 50% aqueous solution of sulfuric acid, was added at 20° C., 23.3 g. of a 70% aqueous solution of hydrogen peroxide over a period of 60 minutes. After a postreaction time of 60 minutes at 20° C., the organic layer was separated, neutralized with 3.0 g. of a 6% aqueous solution of sodium bicarbonate, dried with 1.3 g. of magnesium sulfate dihydrate and filtered. The dried organic layer was then diluted with 7.2 g. of isododecane to provide 55.2 g. of Composition I. Composition I had a total active oxygen content of 11.49% with 3.6% of the total active oxygen being attributable to cyclic ketone peroxides of the formulae I–III.

Preparation of MEKP-Cyclic in Isododecane (Composition II)

To a stirred mixture of 28.8 g. of methylethyl ketone, 13.5 g. isododecane and 14.0 g. of a 70% aqueous solution of sulfuric acid, was added at 40° C., 19.4 g. of a 70% aqueous solution of hydrogen peroxide over a period of 15 minutes. After a postreaction time of 270 minutes at 40° C., the organic layer was separated, neutralized with 12.5 9. of a 6% aqueous solution of sodium bicarbonate, dried with 1.0 g. of magnesium sulfate dihydrate and filtered. The dried organic layer was 42.1 g. of Composition II. Composition II had a total active oxygen content of 10.63% with 96.9% of the total active oxygen being attributable to cyclic ketone peroxides of the formulae I–III.

Preparation of MEKP-Cyclic in Primol® 352 (Composition III)

To a stirred mixture of 28.8 g. of methylethyl ketone, 13.5 g. isododecane and 14.0 g. of a 70% aqueous solution of sulfuric acid, was added at 40° C., 19.4 g. of a 70% aqueous solution of hydrogen peroxide over a period of 20 minutes. After a postreaction time of 120 minutes at 40° C., the organic layer was separated, neutralized with 12.5 g. of a 6% aqueous solution of sodium bicarbonate, dried with 1.0 g. of magnesium sulfate dehydrate and filtered. The dried organic layer was diluted with 2.8 g. of Primol® 352 to provide 45.7 g. of Composition III. Composition III had a total active oxygen content of 10.0% with 97.0% of the total active oxygen being attributable to cyclic ketone peroxides of the formulae I–III.

Preparation of MIPKP-Cyclic in Isododecane (Composition IV)

To a stirred mixture of 17.2 g. of methylisopropyl ketone, 4.0 g. isododecane and 19.6 g. of a 50% aqueous solution of sulfuric acid, was added at 40° C., 9.7 g. of a 70% aqueous solution of hydrogen peroxide over a period of 10 minutes. After a postreaction time of 355 minutes at 40° C., the organic layer was separated and 10.0 g. of water was added. This mixture was then neutralized with 5.5 g. of an aqueous solution of 4N sodium hydroxide and the neutralized organic layer was evaporated in vacuo at 20 mbar and 20° C. The residue was dried with 0.5 g. of magnesium sulfate dehydrate and filtered. The dried organic layer was 12.0 g. of Composition IV. Composition IV had a total active oxygen content of 7.86% with 94.5% of the total active oxygen being attributable to cyclic ketone peroxides of the formulae I–III.

Preparation of MIBKP-Cyclic in Isododecane (Composition V)

To a stirred mixture of 20.0 g. of methylisobutyl ketone, 3.0 g. isododecane and 19.6 g. of a 50% aqueous solution of sulfuric acid, was added at 20° C., 9.7 g. of a 70% aqueous solution of hydrogen peroxide over a period of 15 minutes. After a postreaction time of 300 minutes at 20° C., the temperature was increased to 25° C. for an additional postreaction time of 1080 minutes followed by a temperature increase to 30° C. for a postreaction time of 120 minutes and a temperature increase to 40° C. and a postreaction time of 240 minutes.

Thereafter, the organic layer was separated, neutralized with 15.0 g. of an aqueous solution of 4N sodium hydroxide and stirred for 120 minutes at 40° C. The neutralized organic layer was separated and washed twice with water. The mixture was evaporated in vacuo at 20 mbar and 20° C. The residue still contained two layers. The clear organic layer was decanted and dried with 0.3 g. of magnesium sulfate dehydrate and filtered. The dried organic layer was 11.6 g. of Composition V. Composition V had a total active oxygen content of 8.03% with 93.9% of the total active oxygen being attributable to cyclic ketone peroxides of the formulae I–III.

Preparation of MEKP-cyclic in Primol® 352

To a stirred mixture of 28.8 g methylethyl ketone, 13.5 g Primol 352, and 14.0 g sulfuric acid (70%), 19.4 g of hydrogen peroxide (70%) was added in 20 minutes at 40° C. After a postreaction of 120 minutes at this temperature the organic layer was separated. The organic layer was treated with 10.0 g of a solution of sodium hydrogencarbonate (6%) under stirring for 10 minutes at 20° C. The neutralized organic layer was dried with 1.0 g magnesium sulfate dehydrate and filtrated. The dried organic layer was diluted with 26.4 g Primol 352 resulting in a composition with a weight of 68.3 g.

Preparation of MEKP-cyclic-dimer in Primol® 352

To a stirred mixture of 720 g acetic acid 99%, 97.1 g $H_2O_2$ 70%, 35.2 g water and 7.7 g sulfuric acid 50% was added at 35°–39° C. 144.2 g of methyl ethyl ketone in 25 minutes. After a postreaction of 23 hours at 40° C., the reaction mixture was poured into a stirred mixture of 3 liter of water and 40 g Primol 352. The organic layer was separated after 12 hours and treated 3 times with 50 ml sodium hydroxide 4N for 30 minutes at 30°–40° C. The organic layer was separated and washed 2 times with 50 ml saturated sodium chloride solution at 20° C. The organic layer was dried with magnesium sulfate dehydrate and filtrated. The dried organic layer weighed 70.0 g.

Preparation of MEKP-cyclic-trimer in Primol® 352

To a stirred mixture of 86.5 g methyl ethyl ketone and 66.6 g hydrochloric acid 36% was added at 0°–2° C. 72.6 g of hydrogen peroxide 30% in 20 minutes, followed by a postreaction of 180 minutes at this temperature. Thereafter 200 ml water and 60.0 g Primol 352 were added. The organic layer was separated and treated 3 times with 50 ml sodium hydroxide 4N for 30 minutes at 30°–40° C. The organic layer was separated and washed 2 times with 50 ml saturated sodium chloride solution at 20° C. The organic layer was dried with magnesium sulfate dehydrate and filtrated. The dried organic layer was diluted with 21.9 g Primol 352 and evaporated at 2 mbar and 40° C., weight 114.4 g.

Preparation of MEKP-cyclic-dimer in Pentadecane

To a stirred mixture of 720 g acetic acid 99%, 97.1 g $H_2O_2$ 70%, 35.2 g water and 7.7 g sulfuric acid 50% was added at 25°–37° C. 144.2 g of methylethyl ketone in 30 minutes. After postreactions of 4 hours at 40° C., 12 hours at 20° C. and 7 hours at 40° C., the reaction mixture was poured into a stirred mixture of 3 liter of water and 40 g pentadecane. The organic layer was separated, and treated 2 times with 50 ml sodium hydroxide 4N for 30 minutes at 30° C. The organic layer was separated and washed 2 times with 50 ml saturated sodium chloride solution at 20° C. The organic layer was dried with magnesium sulfate dihydrate and filtrated. The dried organic layer weighed 79.0 g.

Preparation of MEKP-cyclic-trimer in Pentadecane

To a stirred mixture of 144.2 g methylethyl ketone and 92.0 g hydrochloric acid 36% was added at 0°–2° C. 120.1 g of hydrogen peroxide 30% in 30 minutes followed by a postreaction of 180 minutes at this temperature. Thereafter 200 ml water and 80.0 g pentadecane were added. The organic layer was separated and treated 3 times with 50 ml sodium hydroxide 4N for 30 minutes at 30°–40° C. The organic layer was separated and washed 2 times with 50 ml saturated sodium chloride solution at 20° C. The organic layer was dried with magnesium sulfate dehydrate and filtrated. The dried organic layer weighed 168.0 g.

Preparation of MPKP-cyclic in Isododecane

To a stirred mixture of 44.4 g methylpropyl ketone, 20.0 g isododecane and 24.5 g sulfuric acid 50% was added at 40° C. 24.3 g of hydrogen peroxide 70% in 15 minutes, followed by a postreaction of 360 minutes at this temperature. Thereafter the organic layer was separated and treated 3 times 50 ml sodium hydroxide 4N for 30 minutes at 40° C. The organic layer was separated and washed 2 times with 20 ml saturated sodium chloride solution at 20° C. The organic layer was dried with magnesium sulfate dehydrate, filtrated and the filter was washed with 20.0 g isododecane and added to the organic layer. The dried organic layer was diluted with 85.4 g isododecane resulting in a composition with a weight of 132.7 g.

Preparation of MPKP-cyclic-trimer in Primol® 352

To a stirred mixture of 106.5 g methylpropyl ketone and 72.6 g hydrochloric acid 36% was added at 0°–2° C. 72.6 g of hydrogen peroxide 30% in 20 minutes, followed by a postreaction of 180 minutes at this temperature. Thereafter 200 ml water and 50.0 g Primol 352 were added. The organic layer was separated and treated 3 times with 50 ml sodium hydroxide 4N for 30 minutes at 30°–40° C. The organic layer was separated and washed 2 times with 50 ml saturated sodium chloride solution at 20° C. The organic layer was dried with magnesium sulfate dihydrate and filtrated. The dried organic layer was evaporated in vacuo at 2 mbar and 50° C. leaving a composition with a weight of 85.7 g.

Preparation of MPKP-cyclic-dimer in Primol® 352

To a stirred mixture of 720 g acetic acid 99%, 97.1 g $H_2O_2$ 70%, 35.2 g water and 7.7 g sulfuric acid 50% was added at 35°–39° C. of 177.5 g methyl propyl ketone in 25 minutes. After a postreaction of 23 hours at 40° C., the reaction mixture was poured into a stirred mixture of 3 liter of water and 30 9 Primol 352. The organic layer was separated after 12 hours and treated 3 times with 50 ml sodium hydroxide 4N for 30 minutes at 30°–40° C. The organic layer was separated and washed 2 times with 50 ml saturated sodium chloride solution at 20° C. The organic layer was dried with magnesium sulfate dehydrate and filtrated. The dried organic layer was evaporated in vacuo at 2 mbar and 50° C. leaving a composition with a weight of 130.0 g.

Preparation of MPKP-T4/T3 in Isododecane

To a stirred mixture of 105.0 g methylpropyl ketone, 85 g isododecane and 24.0 g sulfuric acid 50% was added at 20° C. 118.5 of hydrogen peroxide 70% in 30 minutes. After a postreaction of 120 minutes at this temperature the organic layer was separated. To the organic layer was added 25.0 g solution of sodium bicarbonate 6%. The reaction mixture was stirred for an additional 15 minutes at this temperature. The obtained organic layer was dried with 25 g magnesium sulfate dihydrate and filtrated. The dried organic layer, weight 199 g. To 112 g of the obtained solution was added 36.8 g isododecane to give a composition with a weight of 148.8 g.

Preparation of MPKP-T3 in Isododecane

To a stirred mixture of 105.0 g methylpropyl ketone, 85 g isododecane and 24.0 g sulfuric acid 50% was added at 20° C. 118.5 g of hydrogen peroxide 70% in 30 minutes. After a postreaction of 120 minutes at this temperature the organic layer was separated. To the organic layer was added 25.0 g solution of sodium bicarbonate 6%. The organic layer was separated. To 97.0 g of the organic layer was dosed 100 g solution of sodium sulfite 20% in 30 minutes at 20° C. The reaction mixture was stirred for an additional 30 minutes at this temperature. The obtained organic layer was washed with 100 ml of water and dried with 10 g magnesium sulfate dehydrate and filtrated. The dried organic layer weighted 76.0 g. To 75.0 g of the obtained solution was added 10.7 g isododecane to give a composition with a weight of 85.7 g.

Preparation of MIPKP-T3 in Solvesso® 100

To a stirred mixture of 126.6 g methylisopropyl ketone, 150 g hexane and 28.2 g sulfuric acid 50% is added at 20° C. 112.2 of hydrogen peroxide 70% in 30 minutes. After a postreaction of 90 minutes at this temperature the organic layer is separated. To the organic layer is added 30.0 g solution of sodium bicarbonate 6% followed by the dosing of 100 g solution of sodium sulfite 20% in 30 minutes at 20° C. The reaction mixture is stirred for an additional 30 minutes at this temperature. The obtained organic layer is washed with 100 ml of water and dried with 15 g magnesium sulfate dehydrate and filtrated. The dried organic layer weighted 281 g. To 150 g of the obtained solution is added 70 g Solvesso 100. The mixture is evaporated in a rotavapor at 20° C. and 10 mbar. The residue had a weight of 136 g.

Preparation of MBKP-cyclic in Isododecane

To a stirred mixture of 40.0 g methylbutyl ketone, 160 g acetic acid 99% and 1.7 g sulfuric acid 50% was added below 30° C. 21.8 g of hydrogen peroxide 70% in 15 minutes. After a postreaction of 480 minutes at 40° C., the reaction mixture was poured in 600 ml water. To the obtained mixture was added 25.0 g isododecane under stirring. Thereafter the organic layer was separated. The organic layer was treated 2 times with 50 ml sodium hydroxide 4N for 30 minutes and thereafter 2 times with 50 ml of water. The organic layer was separated and diluted with 37.5 g isododecane, resulting in a composition with a weight of 80.0 g.

Preparation of MBKP-T4/T3 in Isododecane

To a stirred mixture of 122.0 g methylbutyl ketone, 85 g isododecane and 48.0 g sulfuric acid 50% was added at 30° C. 118.5 of hydrogen peroxide 70% in 30 minutes, subsequently the reaction mixture was cooled to 20° C. in 15 minutes. After a postreaction of 120 minutes at this temperature the organic layer was separated. To the organic layer was added 25.0 g solution of sodium bicarbonate 6%. The reaction mixture was stirred for an additional 15 minutes at this temperature. After separation the obtained organic layer was dried with 25 g magnesium sulfate dehydrate and filtrated. The dried organic layer weight 218 g. To 110 g of the obtained solution was added 37.9 g isododecane to give a composition with a weight of 147.9 g.

Preparation of MBKP-T3 in Isododecane

To a stirred mixture of 122.0 g methylbutyl ketone, 85 g isododecane and 48.0 g sulfuric acid 50% was added at 20° C. 118.5 g of hydrogen peroxide 70% in 30 minutes. After a postreaction of 120 minutes at this temperature the organic layer was separated. To the organic layer was added 25.0 g solution of sodium bicarbonate 6%. The organic layer was separated. To 100.0 g of the organic layer was dosed 100 g solution of sodium sulfite 20% in 30 minutes at 20° C. The reaction mixture was stirred for an additional 30 minutes at this temperature. The obtained organic layer was washed with 100 ml of water and dried with 10 g magnesium sulfate dehydrate and filtrated. The dried organic layer, weight 90.5 g. To 90.0 g of the obtained solution was added 11.3 g isododecane to give a composition with a weight of 101.3 g.

Preparation of DEKP-cyclic in Isododecane

To a stirred mixture of 43.9 g diethyl ketone, 20.0 g isododecane and 24.5 g sulfuric acid 50% was added at 40° C. 24.3 g of hydrogen peroxide 70% in 15 minutes, followed by a postreaction of 360 minutes at this temperature. Thereafter the organic layer was separated. The organic layer was treated 3 times 50 ml sodium hydroxide 4N for 30 minutes. minutes at 40° C. The organic layer was separated and washed 2 times with 20 ml saturated sodium chloride solution at 20° C. The organic layer was dried with magnesium sulfate dihydrate, filtrated and the filter was washed with 5.0 g isododecane and added to the organic layer. The dried organic layer was diluted with 57.0 g isododecane, resulting in a composition with a weight of 119.1 g.

Preparation of DEKP-T4/T3 in Isododecane

To a stirred mixture of 122.0 g diethyl ketone, 85 g isododecane and 48.0 g sulfuric acid 50% was added at 30° C. 118.5 of hydrogen peroxide 70% in 60 minutes. After a postreaction of 120 minutes at this temperature the organic layer was separated. To the organic layer was added 25.0 g solution of sodium bicarbonate 6%. The reaction mixture was stirred for an additional 15 minutes at this temperature. After separation the obtained organic layer was dried with 25 g magnesium sulfate dehydrate and filtrated. The dried organic layer, weight 191 g. To 102 g of the obtained solution was added 28.8 g isododecane to give a composition with a weight of 130.8 g.

Preparation of DEKP-T3 in Isododecane

To a stirred mixture of 122.0 g diethyl ketone, 85 g isododecane and 48.0 g sulfuric acid 50% was added at 20° C. 118.5 g of hydrogen peroxide 70% in 30 minutes. After a postreaction of 120 minutes at this temperature the organic layer was separated. To the organic layer 25.0 g solution of sodium bicarbonate 6% was added. The organic layer was separated. To 100.0 g of the organic layer was dosed 100 g solution of sodium sulfite 20% in 30 minutes at 20° C. The reaction mixture was stirred for an additional 30 minutes at this temperature. The obtained organic layer was washed with 100 ml of water and dried with 10 g magnesium sulfate dihydrate and filtrated. The dried organic layer weight 87.0 g. To 86.0 g of the obtained solution was added 14.1 g isododecane to give a composition with a weight of 101.1 g.

| Analysis of the prepared ketone peroxides | | | | |
|---|---|---|---|---|
| Ketone | Tot % AO | % AO cycl. ket. perox. | D/T GC | % AO linear ket. perox.* |
| MEKP-T3[1] | 11.49 | 0.41 | n.d. | 11.08 |
| MEKP-cyclic[1] | 10.63 | 10.30 | n.d. | 0.33 |
| MEKP-cyclic[2] | 10.92 | 10.59 | n.d. | 0.33 |
| MEKP-cyclic-D[2] | 6.58 | n.d. | 98/2 | n.d |
| MEKP-cyclic-T[2] | 7.06 | n.d. | 2/98 | n.d. |
| MEKP-cyclic-D[3] | 8.56 | n.d. | 98/2 | n.d. |
| MEKP-cyclic-T[3] | 10.11 | n.d. | 2/98 | n.d. |
| MPKP-cyclic[1] | 2.15 | n.d. | 14/86 | n.d. |
| MPKP-cyclic-T[2] | 7.12 | n.d. | 3/97 | n.d. |
| MPKP-cyclic-D[2] | 6.18 | n.d. | 99/1 | n.d. |
| MPKP-T4/T3[1] | 9.0 | 0.07 | n.d. | 8.93 |
| MPKP-T3[1] | 9.0 | 0.27 | n.d. | 8.73 |
| MIPKP-cyclic[1] | 7.86 | 7.42 | n.d. | 0.44 |
| MIPKP-T3[4] | n.d | n.d | n.d. | 8.24 |
| MBKP-cyclic[1] | 2.4 | n.d | 4/96 | n.d. |
| MBKP-T4/T3[1] | 9.0 | 0.63 | n.d. | 8.37 |
| MBKP-T3[1] | 9.0 | 0.42 | n.d. | 8.58 |
| MIBKP-cyclic[1] | 8.03 | 7.54 | n.d. | 0.49 |
| DEKP-cyclic[1] | 2.09 | n.d. | 31/69 | n.d. |
| DEKP-T4/T3[1] | 9.0 | 0.16 | n.d. | 8.84 |
| DEKP-T3[1] | 9.0 | 0.11 | n.d. | 8.89 |

[1]Isododecane
[2]Primol ® 352
[3]Pentadecane
[4]Solvesso ® 100
*Including hydrogen peroxide

EXAMPLES 1–7 AND COMPARATIVE EXAMPLES A–B

In these examples, Moplen® FLS20 was premixed with 0.1 weight percent of Irganox® 1010 antioxidant and the amount of the peroxides mentioned in Table 1 to give an active oxygen concentration of 0.011%. The peroxide was dosed in the form of a liquid formulation. The liquid carrier material for each formulation is given in Table 1. The mixing was performed in a cubic mixer over a period of 15 minutes.

The polypropylene degradation reaction was then carried out in a Haake-Rheocord® System 40 fitted with a twin-screw extruder (Rheomex® TW100 containing intensive mixing screws) at 250° C. and 60 r.p.m. under a nitrogen flush. The degraded polypropylene was granulated and dried at 60° C. before further evaluation. Also two controls were run. The results are given in Table 1.

TABLE 1

Liquid Formulations

| Example | Peroxide | Amount of Peroxide (g/250 g) Polymer | Total Active Oxygen in formulation (%) | Carrier | MFI (g/10 min) |
|---|---|---|---|---|---|
| A | None | — | — | — | 2.3 |
| B | Trigonox® 101 | 0.262 | 10.51 | — | 62 |
| 1 | MEKP-cyclic | 11.700 | 0.26* | Moplen ®FLS 20 PP | 89 |
| 2 | MEKP-cyclic | 0.268 | 10.63 | isododecane | 60 |
| 3 | MEKP-cyclic | 0.568 | 5.01 | isododecane | 71 |
| 4 | MEKP-cyclic | 1.518 | 1.88 | isododecane | 77 |
| 5 | MEKP-cyclic | 7.590 | 0.38 | isododecane | 61 |
| 6 | MEKP-cyclic | 0.284 | 10.00 | white oil | 62 |
| 7 | MEKP-cyclic/ Trigonox® 101 | 0.134/ 0.131 | 10.57 | Trigonox® 101 | 85 |
| Control | | 0 | 0 | isododecane[1] | 2.7 |
| Control | | 0 | 0 | Primol® 352[2] | 5.0 |

[1]1.0 g/100 g PP
[2]0.1 g/100 g PP
*MEKP-Cyclic dissolved in hexane was mixed with Moplen ® FLS 20 PP and the hexane solvent was evaporated.

From Table 1 it can be seen that the cyclic ketone peroxide formulations of the present invention perform as well as commercially available peroxide formulations in the degradation of polypropylene.

EXAMPLES 8–10 AND COMPARATIVE EXAMPLE C

In these examples, the polymer modification process of Example 1 was repeated except that the peroxide was dosed as a solid formulation on the carrier given in Table 2. The results of polypropylene modification with these formulations are given in Table 2.

TABLE 2

Solid Formulations

| Example | Peroxide | Amount of Peroxide (g/250 g Polymer) | Total Active Oxygen in Formulation (%) | Carrier | MFI (g/10 min) |
|---|---|---|---|---|---|
| C | Trigonox® 101-7.5PP-pd | 3.330 | 0.83 | Hostalen® PPU0180P | 64 |
| 8 | MEKP-cyclic | 3.243 | 0.85 | Hostalen® PPU0180P | 70 |
| 9 | MEKP-cyclic | 0.481 | 5.73 | Silica | 56 |
| 10 | MEKP-cyclic | 0.535 | 5.31 | Accurel® PP | 69 |

From Table 2 it can be seen that solid formulations of the present ketone peroxides also perform as well as the commercially available products used in polypropylene degradation.

EXAMPLES 11–13

The procedure of Example 1 was followed in Examples 11–13 to demonstrate that excellent results in polypropylene degradation can be achieved with formulations containing different cyclic ketone peroxides. The formulations and the results obtained are given in Table 3.

TABLE 3

Formulations of Different Cyclic Ketone Peroxides in Isododecane

| Example | Peroxide | Amount of Peroxide (g/100 g Polymer) | Total Active Oxygen in Formulation (%) | MFI (g/10 min) |
|---|---|---|---|---|
| 11 | MEKP-cyclic | 0.107 | 10.62 | 78 |
| 12 | MIPKP-cyclic | 0.149 | 7.86 | 38 |
| 13 | MIBKP-cyclic | 0.146 | 8.03 | 60 |

EXAMPLES 14–18 AND COMPARATIVE EXAMPLES D–E

In these examples, peroxides in accordance with the present invention were formulated in the non-cyclic commercial ketone peroxide Butanox® LPT at different weight ratios. The formulations and the results obtained are given in Table 4.

TABLE 4

Effect of Cyclic/Non-cyclic Ketone Peroxide Ratio

| Example | MEKP-cyclic (g/250 g Polymer) | Butanox ® LPT (g/250 g Polymer) | MEKP-cyclic % of total active Oxygen | Butanox ® LPT % of total active Oxygen | MFI (g/10 min) |
|---|---|---|---|---|---|
| 14 | 0.268 | 0 | 100 | 0 | 78 |
| 15 | 0.254 | 0.016 | 95 | 5 | 77 |
| 16 | 0.201 | 0.081 | 75 | 25 | 54 |
| 17 | 0.134 | 0.162 | 50 | 50 | 37 |
| 18 | 0.067 | 0.243 | 25 | 75 | 20 |
| D | 0.013 | 0.308 | 5 | 95 | 13 |
| E | 0 | 0.324 | 0 | 100 | 9.4 |

*Total Active Oxygen in the polymer employed in the modification process was 0.011%.

From Table 4 it can be seen that excellent degradation results are obtained by the formulations of the present cyclic ketone peroxides in the non-cyclic ketone peroxide Butanox® LPT and that, as the concentration of cyclic ketone peroxide increases, the amount of degradation also increases thereby showing the unexpected advantages of the present formulations over known formulations of non-cyclic ketone peroxides.

EXAMPLE 19

Composition II of the synthesis examples was diluted with isododecane to a total active oxygen content of 4.0%. This diluted composition passed the PVT test with a 9.0 mm orifice demonstrating that it is a safe composition.

EXAMPLE 20

Composition III of the synthesis examples was diluted with Primol® 352 to a total active oxygen content of 7.0%. This diluted composition passed the PVT test with a 9.0 mm orifice demonstrating that it is a safe composition.

EXAMPLE 21

Composition IV of the synthesis examples was diluted with isododecane to a total active oxygen content of 3.0%. This diluted composition passed the PVT test with a 9.0 mm orifice demonstrating that it is a safe composition.

EXAMPLE 22

Composition V of the synthesis examples was diluted with isododecane to a total active oxygen content of 2.0%. This diluted composition passed the PVT test with a 9.0 mm orifice demonstrating that it is a safe composition.

COMPARATIVE EXAMPLE F

The procedure of Example 4 of U.S. Pat. No. 3,649,546 was repeated by mixing 150 g. of methylethyl ketone with 115 g. of the phlegmatizer dimethyl phthalate and 3.0 g. of 50% aqueous solution of sulfuric acid. Then, 159 g. of a 50% aqueous solution of hydrogen peroxide was added over a 10 minute period at 55° C., the reaction was allowed to proceed for 1 hour at 55° C., the products were neutralized with 9.5 g. of sodium hydroxide to a pH of 6.0 and cooled to 28° C. The organic layer (316.3 g.) was then separated from the aqueous layer and the composition was analyzed giving the following results.

TABLE 5

| Component | Organic Layer | Aqueous Layer |
|---|---|---|
| Total Active Oxygen (%) | 8.95 | 8.62 |
| $H_2O_2$ Active Oxygen (%) | 1.41 | 6.85 |
| MEKP-T4 Active Oxygen (%) | 5.03 | 1.77 |
| MEKP-T3 Active Oxygen (%) | 2.30 | — |
| MEKP-Cyclic (%) | 0.21 | — |

This example demonstrates that the procedure of Example 4 of U.S. Pat. No. 3,649,546 produces an organic layer which contains only a small amount (2.3% of the total active oxygen content) of cyclic ketone peroxide. Further, there is no cyclic ketone peroxide in the aqueous layer.

The foregoing examples were presented for the purpose of illustration and description only and are not to be construed as limiting the invention in any way. The scope of the invention is to be determined from the claims appended hereto.

What is claimed is:

1. A transportable, storage stable peroxide composition which comprises 1.0–90% by weight of one or more cyclic ketone peroxides selected from peroxides represented by the formulae I–III:

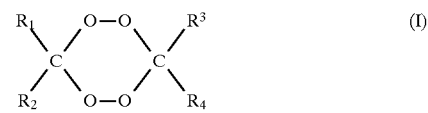

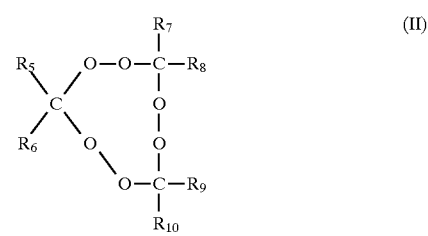

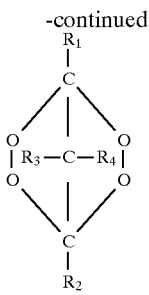

(III)

wherein $R_1$–$R_{10}$ are independently selected from the group consisting of hydrogen, $C_1$–$C_{20}$ alkyl, $C_3$–$C_{20}$ cycloalkyl, $C_6$–$C_{20}$ aryl, $C_7$–$C_{20}$ aralkyl and $C_7$–$C_{20}$ alkaryl, which groups may include linear or branched alkyl moieties; and each of $R_1$–$R_{10}$ may be optionally substituted with one or more groups selected from hydroxy, $C_1$–$C_{20}$ alkoxy, linear or branched $C_1$–$C_{20}$ alkyl, $C_6$–$C_{20}$ aryloxy, halogen, ester, carboxy, nitrile, and amido; and 10–99% by weight of one or more diluents selected from the group consisting of liquid phlegmatizers for the cyclic ketone peroxides, plasticizers, solid polymeric carriers, inorganic supports, organic peroxides and mixtures thereof, with the proviso that when said diluent comprises a non-cyclic ketone peroxide, at least 20% of the total active oxygen content of the formulation must be attributable to one or more cyclic ketone peroxides of the formulae I–III.

2. The composition of claim 1 wherein said liquid solvents and liquid phlegmatizers are selected from the group consisting of alkanols, cycloalkanols, alkylene glycols, alkylene glycol monoalkyl ethers, cyclic ether substituted alcohols, cyclic amides, aldehydes, ketones, epoxides, esters, hydrocarbon solvents, halogenated hydrocarbon solvents, silicone oils, white oils, epoxidized soybean oils, hydrogenated oligomers of alkanes and paraffinic oils.

3. The composition of claim 1 wherein said solid polymeric carriers are selected from the group consisting of polyolefins, ethylene/propylene/diene monomer terpolymers, chlorosulphonated polyethylene, chlorinated polyethylene, polybutylene, polyisobutylene, ethylene/vinyl acetate copolymers, polyisoprene, polybutadiene, butadiene/styrene copolymers, natural rubber, polyacrylate rubber, butadiene/acrylonitrile copolymers, acrylonitrile/butadiene/styrene terpolymers, silicone rubber, polyurethanes, polysulphides, solid paraffins and polycaprolactone.

4. The composition of claim 1 wherein said inorganic supports are selected from the group consisting of fumed silica, precipitated silica, hydrophobic silica, chalk, whiting, surface-treated clays, calcined clays and talc.

5. The composition of claim 1 wherein said liquid phlegmatizers and liquid solvents are selected from the group consisting of monocarboxylic esters of mono- and dihydric alcohols, dicarboxylic acid esters of monohydric alcohols, carbonates of monohydric alcohols, alkoxyalkyl esters, p-keto esters, phthalates, phosphates, benzoates, citrates, adipates, hydrogenated oligomers of alkanes, pentane, heptane, isododecane, amyl benzene, isoamyl benzene, decalin, o-diisopropyl benzene, m-diisopropyl benzene, n-dodecane, 2,4,5,7-tetramethyl octane, n-amyl toluene, 1,2,3,4-tetramethyl benzene, 3,5-diethyl toluene, hexahydronaphthalene, phenyl trichloride, 3-bromo-o-xylene, 4-bromo-o-xylene, 2-bromo-m-xylene, 4-bromo-m-xylene, 5-bromo-m-xylene, o-dibromobenzene, p-dibromobenzene, 1,4-dibromobutane, 1,1-dibromo-2,2-dichloroethane, bromooctane, tetrabromoethylene, 1,2,3-trichlorobenzene, 1,2,4-trichlorobenzene, n-chlorobenzaldehyde, decanal, acetophenone, isophorone, isobutyl ketone, methylphenyl diketone, diamyl ketone, diisoamyl ketone, ethyloctyl ketone, ethylphenyl ketone, acetone, methyl-n-amyl ketone, ethylbutyl ketone, ethylpropyl ketone, methylisoamyl ketone, methylheptyl ketone, methylhexyl ketone, ethylamyl ketone, dimethyl ketone, diethylketone, dipropyl ketone, methylethyl ketone, methylisobutyl ketone, methylisopropyl ketone, methylpropyl ketone, methyl-t-butyl ketone, isobutylheptyl ketone, diisobutyl ketone, 2,4-pentanedione, 2,4-hexanedione, 2,4-heptanedione, 3,5-heptanedione, 3,5-octanedione, 5-methyl-2,4-hexanedione, 2,6-dimethyl-3,5-heptanedione, 2,4-octanedione, 5,5-dimethyl-2,4-hexanedione, 6-methyl-2,4-heptanedione, 1-phenyl-1,3-butanedione, 1-phenyl-1,3-pentanedione, 1,3-diphenyl-1,3-propanedione, 1-phenyl-2,4-pentanedione, methylbenzyl ketone, phenylethyl ketone, methylchloromethyl ketone, methylbromomethyl ketone, styrene oxide and coupling products thereof.

6. The composition of claim 1 wherein said liquid phlegmatizers and liquid solvents are selected from the group consisting of n-butyl alcohol, capryl alcohol, octyl alcohol, dodecyl alcohol, tetrahydrofurfuryl alcohol, 1,4-dihydroxymethyl cyclohexane, cyclohexanol, glycerol, ethylene glycol, polyethylene glycols with molecular weights under 20,000, propylene glycol, dipropylene glycol, neopentyl glycol, hexylene glycol, 1,4-butylene glycol, 2,3-butylene glycol, butene diol, 1,5-pentane diol, 3,6-dimethyloctane-3,6-diol, 2,5-dimethyl-hex-3-yne-2,5-diol, 2,4,7,9-tetramethyldecane-4,7-diol, 2,2,4,4-tetramethyl-1,3-cyclobutanediol, ethylene glycol monoethyl ether, ethylene glycol monobutyl ether, diethylene glycol monoethyl ether, diethylene glycol monobutyl ether, diethylene glycol dibenzoate, dipropylene glycol dibenzoate, propylene glycol dibenzoate, 2-pyrrolidone and N-methyl pyrrolidone.

7. The composition of claim 1 wherein said cyclic ketone peroxide is derived from one or more ketones selected from the group consisting of acetone, acetophenone, methyl-n-amyl ketone, ethylbutyl ketone, ethylpropyl ketone, methylisoamyl ketone, methylheptyl ketone, methylhexyl ketone, ethylamyl ketone, dimethyl ketone, diethylketone, dipropyl ketone, methylethyl ketone, methylisobutyl ketone, methylisopropyl ketone, methylpropyl ketone, methyl-t-butyl ketone, isobutylheptyl ketone, diisobutyl ketone, 2,4-pentanedione, 2,4-hexanedione, 2,4-heptanedione, 3,5-heptanedione, 3,5-octanedione, 5-methyl-2, 4-hexanedione, 2,6-dimethyl-3,5-heptanedione, 2,4-octanedione, 5,5-dimethyl-2,4-hexanedione, 6-methyl-2,4-heptanedione, 1-phenyl-1,3-butanedione, 1-phenyl-1,3-pentanedione, 1,3-diphenyl-1,3-propanedione, 1-phenyl-2,4-pentanedione, methylbenzyl ketone, pheylmethyl ketone, phenylethyl ketone, methylchloromethyl ketone and methylbromomethyl ketone.

8. The composition of claim 1 which further comprises one or more additives selected from the group consisting of anti-caking agents, free-flowing agents, anti-ozonants, antioxidants, anti-degradants, U.V. stabilizers, coagents, fungicides, antistats, pigments, dyes, coupling agents, dispersing aids, blowing agents, lubricants, process-oils and mould-release agents.

9. A method for the modification of (co) polymers which comprises contacting said copolymers with a transportable, storage stable organic peroxide formulation wherein said formulation comprises 1.0–90% by weight of one or more cyclic ketone peroxides selected from peroxides represented by the formulae I–III:

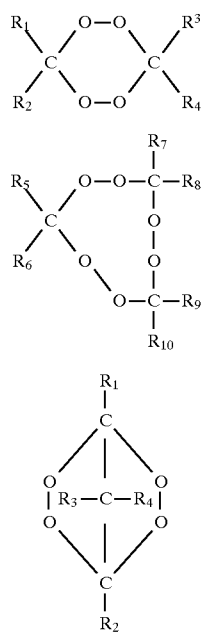

(I)

(II)

(III)

wherein $R_1$–$R_{10}$ are independently selected from the group consisting of hydrogen, $C_1$–$C_{20}$ alkyl, $C_3$–$C_{20}$ cycloalkyl, $C_6$–$C_{20}$ aryl, $C_7$–$C_{20}$ aralkyl and $C_7$–$C_{20}$ alkaryl, which groups may include linear or branched alkyl moieties; and each of $R_1$–$R_{10}$ may be optionally substituted with one or more groups selected from hydroxy, $C_1$–$C_{20}$ alkoxy, linear or branched $C_1$–$C_{20}$ alkyl, $C_6$–$C_{20}$ aryloxy, halogen, ester, carboxy, nitrile, and amido; and 10–99% by weight of one or more diluents selected from the group consisting of liquid phlegmatizers for the cyclic ketone peroxides, plasticizers, solid polymeric carriers, inorganic supports, organic peroxides and mixtures thereof, with the proviso that when said diluent comprises a non-cyclic ketone peroxide, at least 20% of the total active oxygen content of the formulation must be attributable to one or more cyclic ketone peroxides of the formulae I–III.

\* \* \* \* \*